United States Patent
Hu et al.

(10) Patent No.: US 12,103,936 B2
(45) Date of Patent: Oct. 1, 2024

(54) CRYSTAL FORM OF HEPATITIS B SURFACE ANTIGEN INHIBITOR

(71) Applicant: FUJIAN AKEYLINK BIOTECHNOLOGY CO., LTD., Fujian (CN)

(72) Inventors: Yanbin Hu, Shanghai (CN); Fei Sun, Shanghai (CN); Shenyi Shi, Shanghai (CN); Yanxiao Su, Shanghai (CN); Charles Z. Ding, Shanghai (CN)

(73) Assignee: FUJIAN AKEYLINK BIOTECHNOLOGY CO., LTD., Fujian (CN)

( * ) Notice: Subject to any disclaimer, the term of this patent is extended or adjusted under 35 U.S.C. 154(b) by 712 days.

(21) Appl. No.: 17/293,479

(22) PCT Filed: Nov. 22, 2019

(86) PCT No.: PCT/CN2019/120169
§ 371 (c)(1),
(2) Date: May 13, 2021

(87) PCT Pub. No.: WO2020/103924
PCT Pub. Date: May 28, 2020

(65) Prior Publication Data
US 2022/0017536 A1   Jan. 20, 2022

(30) Foreign Application Priority Data
Nov. 22, 2018  (CN) .......................... 201811399514.3

(51) Int. Cl.
*C07D 498/04*   (2006.01)
(52) U.S. Cl.
CPC ........ *C07D 498/04* (2013.01); *C07B 2200/13* (2013.01)
(58) Field of Classification Search
CPC ........ A61P 1/16; A61P 31/12; C07B 2200/13; C07D 498/04
See application file for complete search history.

(56) References Cited

U.S. PATENT DOCUMENTS 7,307,073 B2   12/2007   Grove et al.

FOREIGN PATENT DOCUMENTS

| CN | 108884107 A | 11/2018 |
|---|---|---|
| RU | 2279434 C2 | 7/2006 |

(Continued)

OTHER PUBLICATIONS

Feb. 1, 2023 the main rejection of the Decision of refusal issued in Russian Patent Application No. 2021117776.

(Continued)

*Primary Examiner* — Savitha M Rao
(74) *Attorney, Agent, or Firm* — Houston Beshining Law Office PLLC; Liangang Ye

(57) ABSTRACT

The present invention discloses a crystal form of a hepatitis B surface antigen inhibitor and a preparation method therefor, and also comprises the use of the crystal form in preparing the hepatitis B surface antigen inhibitor.

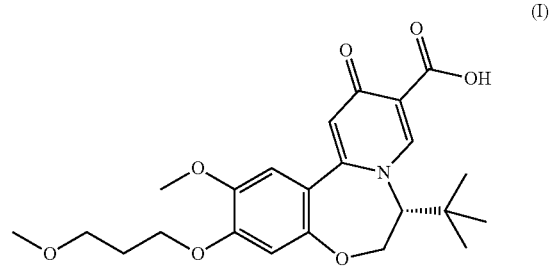

(I)

6 Claims, 5 Drawing Sheets
Specification includes a Sequence Listing.

(56) References Cited

FOREIGN PATENT DOCUMENTS

| WO | 2018022282 A1 | 2/2018 |
| WO | 2018085619 A1 | 5/2018 |
| WO | 2018214875 A1 | 11/2018 |

OTHER PUBLICATIONS

Jun. 19, 2023 1st Office Action issued on corresponding KR 10-2021-7019055.
International Search Report of PCT/CN2019/120169 dated Feb. 19, 2020.
Written Opinion of The International Searching Authority of PCT/CN2019/120169 dated Feb. 19, 2020.
1st OA of TW108142579 dated Nov. 4, 2020.
Priority application CN201811399514.3.
Jun. 6, 2022 Russian Office Action issued in Russian Patent Application No. 2021117776.
Aug. 5, 2022 Canadian Office Action issued in Canadian Patent Application No. 3,120,532.
Dec. 24, 2021 the First Office Action issued in Chinese application No. 2019800423596.
Jan. 4, 2022 the EESR issued in European application No. 19887009.9.
Jan. 20, 2022 the First Office Action issued in Russian application No. 2021117776.
Mino R. Caira "Crystalline Polymorphism of Organic Compounds", Topics in Current Chemistry, 1998, vol. 198, p. 163-208, p. 164-167, section 1, p. 164 first paragraph.
Jan. 16, 2024 issued Refusal Issued for a corresponding RU Patent Application No. 2021117776.

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Forward primer sequence

<400> SEQUENCE: 1
gtgtctgcgg cgttttatca                                              20

<210> SEQ ID NO 2
<211> LENGTH: 21
<212> TYPE: DNA
<213> ORGANISM: Artificial Sequence
```

```
-continued

<220> FEATURE:
<223> OTHER INFORMATION: Reverse primer sequence

<400> SEQUENCE: 2
gacaaacggg caacatacct t                                             21

<210> SEQ ID NO 3
<211> LENGTH: 28
<212> TYPE: DNA
<213> ORGANISM: Artificial Sequence
<220> FEATURE:
<223> OTHER INFORMATION: Probe nucleotide sequence

<400> SEQUENCE: 3
cctctkcatc ctgctgctat gcctcatc                                      28
```

CRYSTAL FORM OF HEPATITIS B SURFACE ANTIGEN INHIBITOR

The Sequence Listing is submitted concurrently with the specification as an ASCII formatted text file via EFS-Web, with a file name of "P21413872US-2-SEQ.txt", a creation date of Apr. 25, 2021, and a size of 860 bytes. The Sequence Listing filed via EFS-Web is part of the specification and is incorporated in its entirety by reference herein.

The present application is a National Stage of International Application No. PCT/CN2019/120169, filed on Nov. 22, 2019, which claims priority of the Chinese Patent Application No. CN201811399514.3 filed on Nov. 22, 2018, the contents of which are incorporated herein by reference in its entirety.

TECHNICAL FIELD

The present disclosure relates to a crystal form of a hepatitis B surface antigen inhibitor and a preparation method therefor, and also comprises the use of the crystal form in preparing the hepatitis B surface antigen inhibitor.

BACKGROUND

Viral hepatitis B, hepatitis B for short, is a disease caused by Hepatitis B Virus (HBV for short) infection in the body. Hepatitis B virus is a hepatotropic virus that mainly exists in hepatocytes and causes damages to the hepatocytes, resulting in inflammation, necrosis and fibrosis of the hepatocytes. Viral hepatitis B is divided into two types, acute hepatitis B and chronic hepatitis B. Acute hepatitis B may be mostly self-healing in adults through their inherent immune mechanism. However, chronic hepatitis B (CHB) has become a major challenge for global health care, and a leading cause of chronic liver diseases, cirrhosis and hepatocellular carcinoma (HCC). It is estimated that 2 billion people worldwide are infected with chronic hepatitis B virus, and more than 350 million people have developed hepatitis B. Every year, approximately 600,000 people die for the complications of chronic hepatitis B. China is a high-prevalence area of hepatitis B, with many accumulated patients with hepatitis B, which is a serious hazard. According to the data, there are about 93 million people infected with hepatitis B virus in China, and about 20 million of them are diagnosed with hepatitis B, 10%-20% of which can develop into cirrhosis, and 1%-5% of which can develop into hepatocellular carcinoma.

The key to a functional cure for hepatitis B is the elimination of HBsAg (hepatitis B virus surface antigen) and the production of surface antibodies. Quantification of HBsAg is a very important biological indicator. A reduction and seroconversion of HBsAg are rarely observed in patients with chronic infection, which is the endpoint of current therapies.

The surface antigen protein of hepatitis B virus (HBV) plays a very important role in the invasion of HBV into hepatocytes, and is of great significance for the prophylaxis and treatment of HBV infection. Surface antigen proteins include large (L), medium (M) and small (S) surface antigen proteins that share a common C-terminal S region. They are expressed by a same open reading frame, and their different lengths are determined by the three AUG start codons of the reading frame. These three surface antigen proteins include pre-S1/pre-S2/S, pre-S2/S and S domains. HBV surface antigen proteins are integrated into the endoplasmic reticulum (ER) membrane, which is initiated by the N-terminal signal sequence. They not only constitute the basic structure of virions, but also form globular and filamentous subviral particles (SVPs, HBsAg) that accumulate in ER, host ER and pre-Golgi apparatus, and SVP contains most S surface antigen proteins. L protein is critical in the morphogenesis of the virus and the interaction of the nucleocapsid, but is not necessary for the formation of SVP. Due to the absence of nucleocapsids, the SVPs described above are non-infectious. SVPs are greatly involved in disease progression, especially in the immune response to hepatitis B virus. In the blood of infected individuals, the amount of SVPs is at least 10,000 times the amount of the virus, trapping the immune system and thus weakening the body's immune response to hepatitis B virus. HBsAg also inhibits human innate immunity with its ability to inhibit the production of cytokines induced by polysaccharides (LPS) and IL-2, the function of dendritic cells (DCs) and the induction activity of ERK-1/2, and kinase-1/2 of c-Jun N-terminus in monocytes interfered by LPS. It is worth noting that the disease progression in cirrhosis and hepatocellular carcinoma is also largely associated with persistent secretion of HBsAg. These findings suggest that HBsAg plays an important role in the development of chronic hepatitis B.

The anti-HBV drugs that have been approved for marketing to date are mainly immunomodulators (interferon-α, and peg-interferon-α-2α) and antiviral therapeutic drugs (Lamivudine, Adeforvir, Dipivoxil, Entecavir, Telbivudine, Tenofovir, Clevudine, etc.). Among them, the antiviral therapeutic drugs belong to nucleotide drugs, whose mechanism of action is to inhibit the synthesis of HBV DNA and is not able to reduce HBsAg level directly. As with the extended therapy, nucleotide drugs show HBsAg elimination at a rate similar to natural observations.

Clinically available therapies exhibit a poor efficacy in reducing HBsAg. Therefore, the development of oral small molecule inhibitors that can effectively reduce HBsAg is now urgently needed for clinical use.

Roche has developed a surface antigen inhibitor named RG7834 for the treatment of hepatitis B, and reported the efficacy of this compound in the woodchuck model against hepatitis B: RG7834 can reduce surface antigens by 2.57 Log and HBV-DNA by 1.7 Log when it was used as a single drug. The compound exhibits good activity, but it is necessary to separate isomers in the process of molecular synthesis, which reduces the yield and increases the cost.

WO2017013046A1 discloses a series of 2-oxo-7,8-dihydro-6H-pyrido[2,1,a][2]benzazepine-3-carboxylic acid derivative for the treatment or prophylaxis of hepatitis B virus infection. The highest activity among this series of fused ring compounds in Embodiment 3 has an $IC_{50}$ of 419 nM, which can be further improved greatly in activity. This series of compounds contain chiral centers, which is difficult to synthesize asymmetrically. Generally, the 7-membered carbon ring has a poor aqueous solubility and is susceptible to be metabolized by oxidation.

CONTENT OF THE PRESENT INVENTION

The present disclosure provides a crystal form A of a compound of formula (I) having a X-ray powder diffraction pattern comprising characteristic diffraction peaks with following angles 2θ: 8.04°±0.2°, 16.52°±0.2° and 19.52°±0.2°,

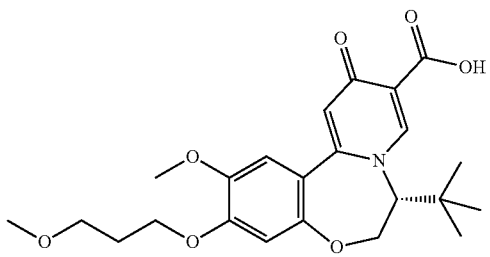 (I)

In some embodiments of the present disclosure, the X-ray powder diffraction pattern of the crystal form A as defined above comprises characteristic diffraction peaks with following angles 2θ: 8.04°±0.2°, 10.47°±0.2°, 11.90°±0.2°, 16.52°±0.2°, 18.06°±0.2°, 19.52°±0.2°, 22.02°±0.2° and 25.28°±0.2°.

In some embodiments of the present disclosure, the X-ray powder diffraction pattern of the crystal form A as defined above is shown in FIG. 1.

In some embodiments of the present disclosure, the analysis data of the XRPD pattern of the crystal form A as defined above is shown in Table 1.

TABLE 1

Analytical data of the XRPD pattern of the crystal form A of the compound of formula (I)

| No. | Angle 2θ (°) | d-spacing (Å) | Intensity | Relative intensity (%) |
|---|---|---|---|---|
| 1 | 3.983 | 22.1684 | 73 | 2.0 |
| 2 | 8.041 | 10.9871 | 3718 | 100.0 |
| 3 | 9.918 | 8.9113 | 204 | 5.5 |
| 4 | 10.474 | 8.4390 | 690 | 18.5 |
| 5 | 11.658 | 7.5845 | 383 | 10.3 |
| 6 | 11.896 | 7.4336 | 955 | 25.7 |
| 7 | 14.759 | 5.9974 | 93 | 2.5 |
| 8 | 15.822 | 5.5967 | 551 | 14.8 |
| 9 | 16.120 | 5.4937 | 404 | 10.9 |
| 10 | 16.521 | 5.3613 | 1601 | 43.1 |
| 11 | 17.499 | 5.0638 | 615 | 16.5 |
| 12 | 18.059 | 4.9081 | 1013 | 27.2 |
| 13 | 19.518 | 4.5443 | 1692 | 45.5 |
| 14 | 20.020 | 4.4316 | 1172 | 31.5 |
| 15 | 20.179 | 4.3971 | 1286 | 34.6 |
| 16 | 21.025 | 4.2219 | 74 | 2.0 |
| 17 | 21.683 | 4.0953 | 827 | 22.2 |
| 18 | 22.019 | 4.0336 | 1792 | 48.2 |
| 19 | 22.881 | 3.8836 | 166 | 4.5 |
| 20 | 23.160 | 3.8373 | 202 | 5.4 |
| 21 | 23.863 | 3.7258 | 108 | 2.9 |
| 22 | 24.659 | 3.6074 | 511 | 13.8 |
| 23 | 25.281 | 3.5201 | 1652 | 44.4 |
| 24 | 25.580 | 3.4796 | 1260 | 33.9 |
| 25 | 25.719 | 3.4610 | 1464 | 39.4 |
| 26 | 26.421 | 3.3707 | 340 | 9.2 |
| 27 | 26.820 | 3.3214 | 564 | 15.2 |
| 28 | 27.020 | 3.2973 | 401 | 10.8 |
| 29 | 27.899 | 3.1954 | 844 | 22.7 |
| 30 | 28.415 | 3.1385 | 94 | 2.5 |
| 31 | 28.923 | 3.0845 | 203 | 5.5 |
| 32 | 29.260 | 3.0497 | 166 | 4.5 |
| 33 | 29.823 | 2.9935 | 92 | 2.5 |
| 34 | 30.661 | 2.9135 | 47 | 1.3 |
| 35 | 31.640 | 2.8255 | 225 | 6.1 |
| 36 | 32.619 | 2.7430 | 132 | 3.5 |
| 37 | 33.241 | 2.6931 | 112 | 3.0 |
| 38 | 34.760 | 2.5788 | 89 | 2.4 |
| 39 | 35.519 | 2.5254 | 104 | 2.8 |
| 40 | 35.979 | 2.4942 | 88 | 2.4 |
| 41 | 36.538 | 2.4573 | 67 | 1.8 |
| 42 | 37.912 | 2.3713 | 51 | 1.4 |
| 43 | 38.600 | 2.3306 | 134 | 3.6 |
| / | / | / | / | / |

In some embodiments of the present disclosure, the crystal form A as defined above has a differential scanning calorimetry curve with an onset of endothermic peak at 139.64±5° C.

In some embodiments of the present disclosure, the pattern of differential scanning calorimetry curve of the crystal form A as defined above is shown in FIG. 2.

In some embodiments of the present disclosure, the crystal form A as defined above has a thermogravimetric analysis curve with a weight loss of 0.4757% at 125 0.23±3° C.

In some embodiments of the present disclosure, the pattern of thermogravimetric analysis curve of the crystal form A as defined above is shown in FIG. 3.

The present disclosure also provides a use of the crystal form A as defined above in the preparation of a medicament for treating Hepatitis B.

Technical Effects

The compounds of the present disclosure has significant activity of anti-hepatitis B virus. The compounds of the present disclosure have a moderate plasma protein binding rate without inhibiting cytochrome P450 isoenzyme, thereby exhibiting a low risk of drug-drug interaction; exhibit excellent stability in the liver microsomes in three species, rats, human and mice, indicating that the compounds are not easily metabolized; have good exposure and bioavailability; exhibit a good tolerance in the single-dose neurotoxicity test. The synthetic process of the compounds of the present disclosure is simple and economical.

The crystal form of the present disclosure have good solubility of crystal form, and is easy to prepare, with good physical stability and chemical stability.

DEFINITIONS AND EXPLANATIONS

Unless otherwise indicated, the following terms and phrases used in this document are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The intermediate compounds of the present disclosure can be prepared by various synthetic methods known to those skilled in the art, including the specific embodiments described below, the embodiments formed by combining the embodiments described below with other chemical synthesis methods, and equivalent alternatives well-known for those skilled in the art. Preferred embodiments include, but are not limited to the embodiments of the present disclosure.

The chemical reactions in the embodiments of the present disclosure are carried out in an appropriate solvent, which is suitable for the chemical change and the required reagents and materials of the present disclosure. In order to obtain the compounds of the present disclosure, it is sometimes necessary for those skilled in the art to modify or select the synthetic steps or reaction processes based on the existing embodiments.

The present disclosure will be specifically described below by way of embodiments, but the scope of the present disclosure is not limited thereto.

All solvents used in the present disclosure are commercially available and can be used without further purification.

Compounds are named manually or by ChemDraw® software, and the commercially available compounds are named using their vendor directory names.

X-Ray Powder Diffractometer (XRPD) Method of the Present Disclosure

Model: DX-2700BH X-ray diffractometer (Haoyuan Instrument Co., Ltd.)

Testing Method: About 10-20 mg of sample was used for XRPD detection.

The detailed XRPD parameters are as follows:

X-ray tube: Cu, kα, (λ=1.54184 Å).

X-ray tube voltage: 40 kV, X-ray tube current: 30 mA

Divergence slit: 1 mm

Detector slit: 0.3 mm

Anti-scattering slit: 1 mm

Scanning range: 3-40 deg

Step size: 0.02 deg

Step time: 0.5 second

Differential Scanning Calorimeter (DSC) Method of the Present Disclosure

Model: METTLER TOLEDO DSC1 Differential Scanning calorimeter

Testing Method: 2-6 mg of sample was placed in 30 UL DSC gold-plated high-pressure crucible for testing, by increasing the temperature of sample from 40° C. to 350° C. at a rate of 10° C./min.

Thermal Gravimetric Analyzer (TGA) Method of the Present Disclosure

Model: TA TGA550 Thermal Gravimetric Analyzer

Testing method: 2-10 mg of sample was placed in the aluminum crucible, then was placed in the platinum hanging basket for testing, and heated at a rate of 10° C./min with 40 mL/min of gas flow rate under $N_2$ to increase the temperature of sample from 40° C. to 500° C.

DETAILED DESCRIPTION OF THE PREFERRED EMBODIMENT

Figure 1:
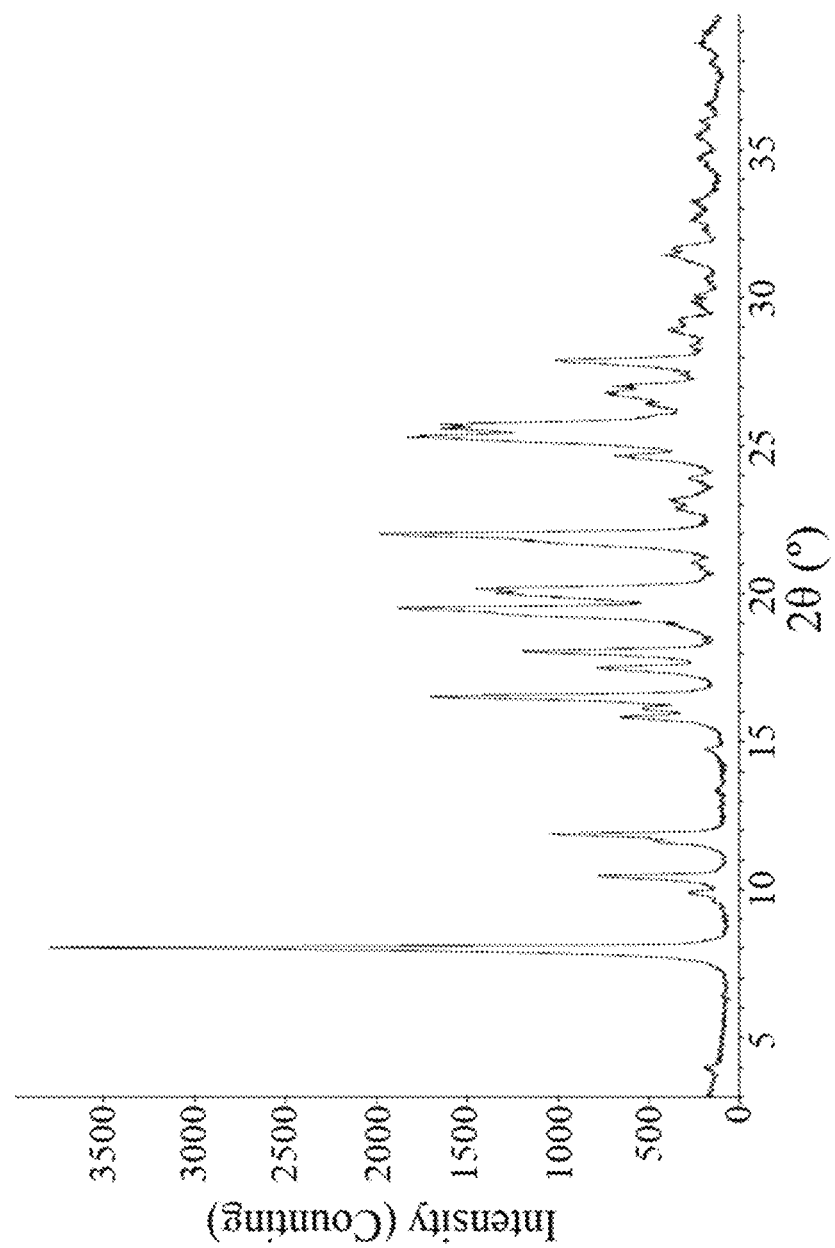
FIG. 1 is the XRPD pattern of the crystal form A of the compound of formula (I) using Cu-Kα radiation.
Figure 2:
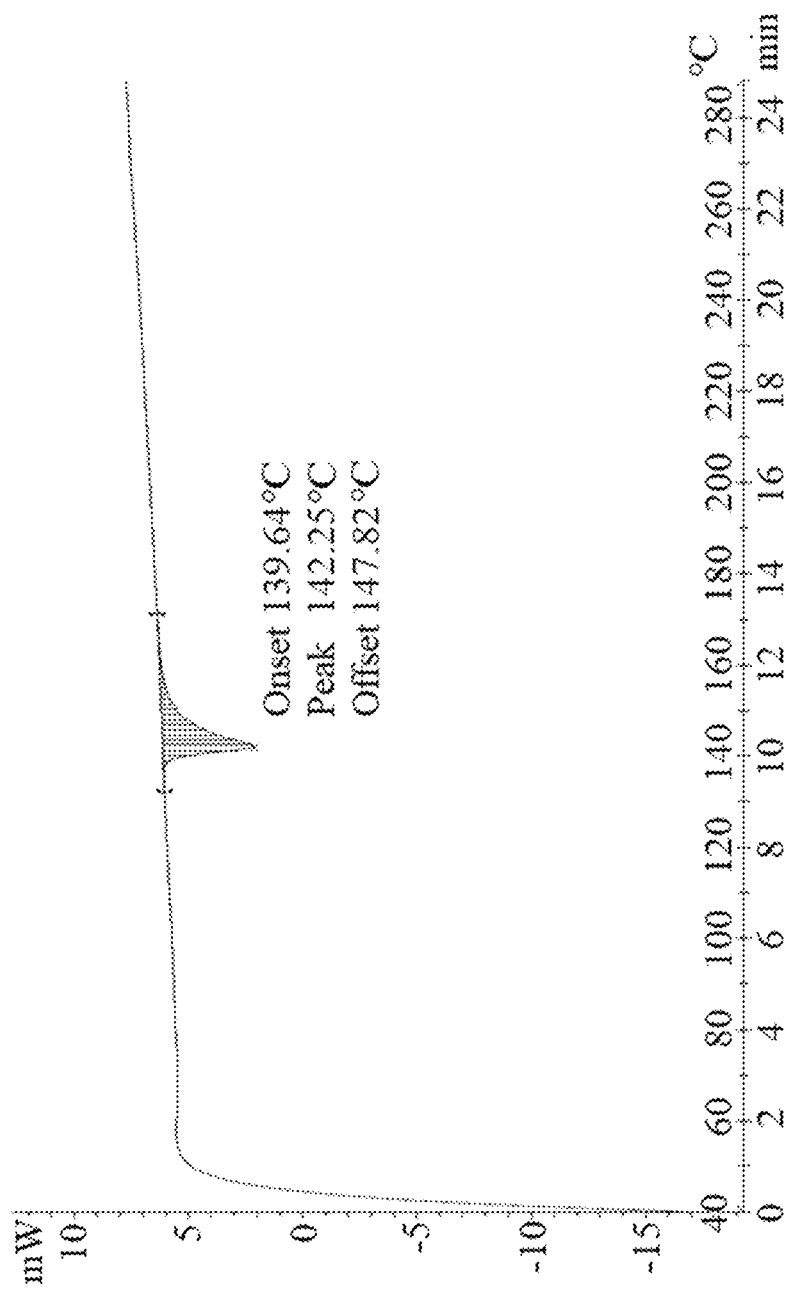
FIG. 2 is the DSC pattern of the crystal form A of the compound of formula (I).
Figure 3:
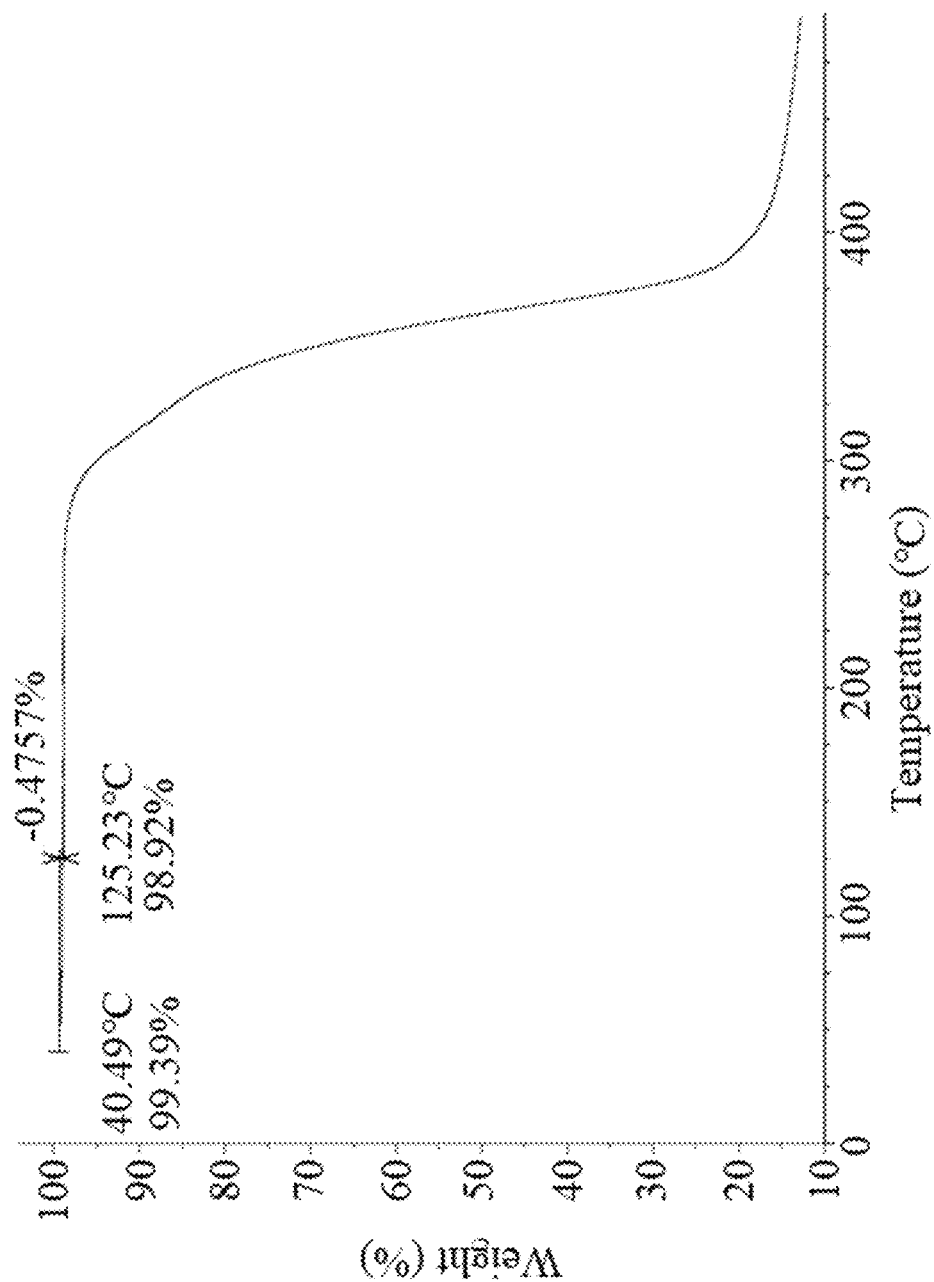
FIG. 3 is the TGA pattern of the crystal form A of the compound of formula (I).

In order to better understand the contents of the present disclosure, the following embodiments further illustrate the present disclosure, but the present disclosure is not limited thereto.

Example 1 Preparation of the Compound of Formula (I)

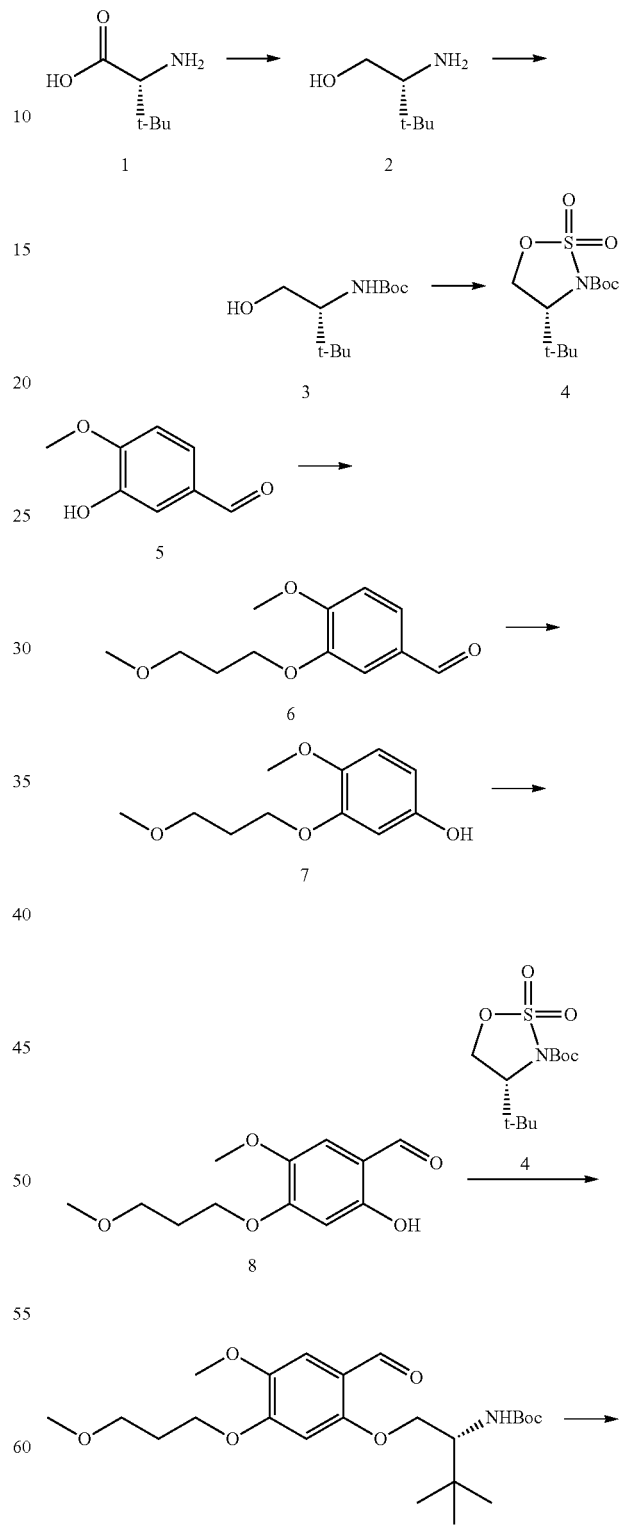

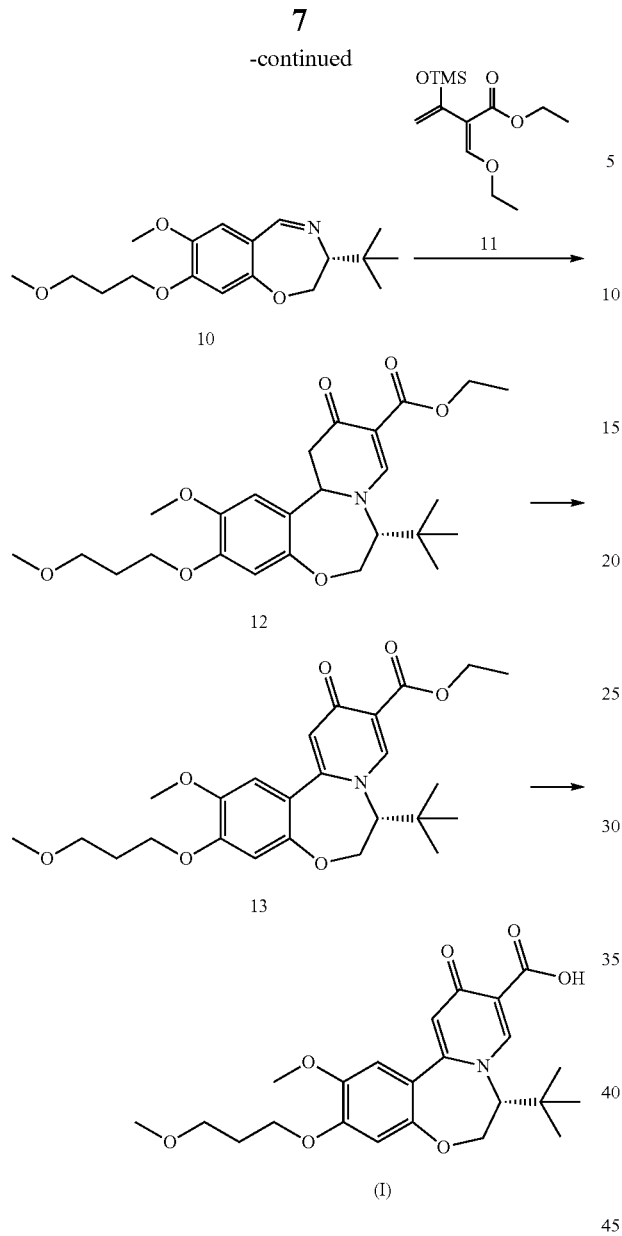

Step A: Lithium aluminum hydride (80.00 g, 2.11 mol, 2.77 eq.) was added into the tetrahydrofuran (400.00 mL) solution containing compound 1 (100.00 g, 762.36 mmol, 1.00 eq.) at 0° C. The mixture was stirred for 10 hrs at 10° C. Then 80.00 mL of water was firstly added into the reaction solution when stirring, followed by adding 240.00 mL of 15% NaOH solution and 80.00 mL of water. The resulting suspension was stirred for 20 min at 10° C., and colorless clear solution was obtained by filtration. Compound 2 was obtained after being concentrated under vacuum.

Step B: Compound 2 (50.00 g, 426.66 mmol) and triethylamine (59.39 mL, 426.66 mmol) were dissolved in dichloromethane (500.00 mL). Then the solution of di-tert-butyl dicarbonate (92.19 g, 422.40 mmol) in dichloromethane (100.00 mL) was added dropwise into the above reaction solution. Then the reaction mixture was stirred for 12 hrs at 25° C. After that, the reaction solution was washed by brine (600.00 mL), and dried with anhydrous sodium sulfate. The organic phase was concentrated under vacuum and spin dried, followed by recrystallization with methyl tertiary-butyl ether/petroleum ether (50.00/100.00) to give Compound 3.

Step C: Thionyl chloride (100.98 mL, 1.39 mmol) was dissolved in acetonitrile (707.50 mL), then the solution of Compound 3 (121.00 g, 556.82 mmol) in acetonitrile (282.90 mL) was added dropwise into the above reaction solution at −40° C. After addition, pyridine (224.72 mL, 2.78 mol) was added into the reaction solution at one time. Next, the ice bath was removed and the reaction solution was stirred for 1 hr at 5-10° C. After the solvent was concentrated under vacuum, ethyl acetate (800.00 mL) was added to allow the solid to precipitate, followed by filtering, and the filtrate was concentrated under vacuum. The second step: the resulting oil water and ruthenium trichloride (12.55 g, 55.68 mmol) were dissolved in acetonitrile (153.80 mL). The suspension of sodium periodate (142.92 g, 668.19 mmol) in water (153.80 mL) was slowly added into the reaction solution described above. The final reaction mixture was stirred for 0.15 hr at 5-10° C. The reaction mixture was filtered and the filtrate was obtained. The filtrate was extracted with ethyl acetate (800.00 mL×2), and the organic phase was washed with brine (800.00 mL), dried with anhydrous sodium sulfate, filtered and concentrated under vacuum. Compound 4 was obtained from purification by column chromatograph (SiO$_2$, petroleum ether/ethyl acetate=50/1-20/1).

Step D: Compound 5 (100.00 g, 657.26 mmol) was dissolved in acetonitrile (1300.00 mL), and K$_2$CO$_3$ (227.10 g, 1.64 mol) and 1-Br-methoxypropane (110.63 g, 722.99 mmol) were added. The reaction solution was stirred for 6 hrs at 85° C. The reaction solution was extracted with 600.00 mL of ethyl acetate (200.00 mL×3), dried with anhydrous sodium sulfate, then filtered and concentrated under vacuum to give Compound 6.

Step E: Compound 6 (70.00 g, 312.15 mmol) was dissolved in dichloromethane, and m-chloroperoxybenzoic acid (94.27 g, 437.01 mmol) was added. The mixture was stirred for 2 hrs at 50° C. After cooling, the reaction solution was filtered, and the filtrate was extracted with dichloromethane. The organic phase was washed with saturated 2000.00 mL of NaHCO$_3$ solution (400.00 mL×5), dried with anhydrous sodium sulfate, and concentrated under vacuum. The resulting brown oily product was dissolved with methanol as little as possible, and then 2 mol/L of KOH solution (350.00 mL) was added slowly (the process is exothermetic). The black reaction solution was stirred for 20 min at room temperature, then the pH was adjusted to 5 with 37% HCl. The reaction solution was extracted with 400 mL of ethyl acetate (200.00 mL×2), and the organic phase was washed with 200.00 mL of brine (100.00 mL×2), dried with anhydrous sodium sulfate, and concentrated under vacuum to give Compound 7.

Step F: Compound 7 (33.00 g, 155.48 mmol) was dissolved in THF (330.00 mL), then paraformaldehyde (42.02 g, 466.45 mmol), MgCl$_2$ (29.61 g, 310.97 mmol), and triethylamine (47.20 g, 466.45 mmol, 64.92 mL) were added. The reaction solution was stirred for 8 hrs at 80° C. After the reaction was finished, the reaction solution was quenched with 2 mol HCl solution (200.00 mL) at 25° C., then extracted with 600.00 mL of ethyl acetate (200.00 mL×3). The organic phase was washed with 400.00 mL of brine (200.00 mL×2), dried with anhydrous sodium sulfate, and concentrated under vacuum to give the residue. The residue was washed with ethanol (30.00 mL), filtered to give a filter cake as Compound 8.

Step G: Compound 8 (8.70 g, 36.21 mmol) was dissolved in N,N-dimethyl formamide (80.00 mL), then $K_2CO_3$ (10.01 g, 72.42 mmol) and compound 4 (11.13 g, 39.83 mmol) were added. The reaction mixture was stirred for 2 hrs at 50° C. After that, the reaction solution was quenched with 1.00 mol/L aqueous hydrochloric acid (200.00 mL), and extracted with dichloromethane (150.00 mL×2). The organic phases were combined, washed with water (150.00 mL×3) and dried with anhydrous sodium sulfate, then filtered and concentrated under vacuum to obtain Compound 9.

Step H: Compound 9 (15.80 g, 35.95 moll) was dissolved in dichloromethane (150.00 mL), and trifluoroacetic acid (43.91 mL, 593.12 mmol) was added. The reaction solution was stirred for 3 hrs at 10° C. The reaction solution was concentrated under vacuum to give a residue. The residue was added with $NaHCO_3$ solution (100.00 mL), and extracted with dichloromethane (100.00 mL). The organic phase was dried with anhydrous sodium sulfate, filtered and concentrated under vacuum to obtain Compound 10.

Step I: Compound 10 (5.00 g, 15.56 mmol) was dissolved in toluene (20.00 mL), and compound 11 (8.04 g, 31.11 mmol) was added. The reaction solution was stirred for 12 hrs at 120° C. under $N_2$ atmosphere. After that, the reaction solution was quenched with water (100.00 mL), and extracted with ethyl acetate (100.00 mL×2). The organic phases were combined, washed with water (80.00 mL×2), and dried with anhydrous sodium sulfate, then filtered and concentrated under vacuum. The residue was purified with reversed phase column, and then purified with HPLC (Column: Phenomenex luna C18 250×50 mm×10 μm; Mobile phase: [water (0.225% formic acid)-acetonitrile]; Elution gradient: 35%-70%, 25 min) to give Compound 12.

Step J: Compound 12 (875.00 mg, 1.90 mmol) was dissolved in toluene (20.00 mL) and 1,2-dimethoxyethane (20.00 mL), then tetrachloro-benzoquinone (1.40 g, 5.69 mmol) was added. The reaction solution was stirred for 12 hrs at 120° C. The reaction solution was cooled to room temperature, then saturated $Na_2CO_3$ solution (50.00 mL) and ethyl acetate (60.00 mL) were added. The mixture was stirred for 20 min at 10-15° C., and separated for the organic phase. The organic phase was added with 2.00 mol/L of HCl solution (60.00 mL), then stirred for 20 min at 10-15° C., and separated. The separated organic phase was washed again with 2 mol/L of HCl solution (60.00 mL×2), separated, then 2 mol/L of NaOH solution (200.00 mL) and dichloromethane (200.00 mL) were added into the water phase, and then separated. The organic phase was dried with anhydrous sodium sulfate, filtered and concentrated under vacuum to give Compound 13.

Step K: Compound 13 (600.00 mg, 1.31 mmol) was dissolved in methanol (6.00 mL), and 4.00 mol/L of NaOH solution (2.00 mL, 6.39 eq.) was added. The reaction solution was stirred for 0.25 hr at 15° C. The pH of the reaction solution was adjusted to 3-4 with 1.00 mol/L of HCl solution, then the reaction solution was extracted with dichloromethane (50.00 mL×3). The organic phases were combined and washed with brine (50.00 mL), and dried with anhydrous sodium sulfate, then filtered and concentrated under vacuum to give the compound of formula (I). ee value (enantiomeric excess): 100%.

SFC (Supercritical Fluid Chromatography) method:
Column: Chiralcel OD-3 100 mm×4.6 mm, I.D., 3 μm.
Mobile Phase: 5%-40% methanol (0.05% diethylamine) in $CO_2$.
Flow rate: 3 mL/min.
Wavelength: 220 nm.

Example 2 Preparation of Crystal Form a of the Compound of Formula (I)

Step A: The compound of formula (I) (1.89 kg) was added into ethanol (9.5 L), then heated refluxed to be dissolved, followed by gradient cooling. When the reaction system was cooled down to about 25° C., a great amount of solid was precipitated, followed by filtration to obtain the solid.

Step B: The solid obtained in Step A was added into water (9.5 L), and stirred for 3-5 hrs at room temperature, then filtered to obtain the solid.

Step C: The solid obtained in Step B was dried for 48-72 hrs in the oven at 45-50° C., to obtain the crystal form A of the compound of formula (I). Mass spectrum: $[M+H]^+$=432.2. $^1$H NMR (400 MHz, $CDCl_3$) δ 15.72 (br s, 1H), 8.32-8.93 (m, 1H), 6.60-6.93 (m, 2H), 6.51 (br s, 1H), 4.38-4.63 (m, 2H), 4.11 (br dd, J=4.52, 12.23 Hz, 3H), 3.79-3.87 (m, 3H), 3.46-3.54 (m, 2H), 3.29 (s, 3H), 2.07 (quin, J=6.24 Hz, 2H), 0.77-1.21 (m, 9H).

Example 3 HBV In Vitro Test of the Compound of Formula (I)

Experimental Materials:
1. Cell Line: HepG2.2.15 Cells
    HepG 2.2.15 cell culture medium (DMEM/F12, Invitrogen-11330032; 10% serum, Invitrogen-10099141; 100 units/mL penicillin and 100 μg/mL streptomycin, Hyclone-SV30010; 1% non-essential amino acids, Invitrogen 11140050; 2 mm L-glutamine, Invitrogen-25030081; 300 μg/mL Geneticin, Invitrogen-10131027)
2. Reagents:
    Pancreatin (Invitrogen-25300062)
    DPBS (Corning-21031CVR)
    DMSO (Sigma-D2650-100 mL)
    High-throughput DNA purification kit (QIAamp 96 DNA Blood Kit, Qiagen-51162)
    Quantitative quick start universal probe reagent (FastStart Universal Probe Master, Roche-04914058001)
    Hepatitis B surface antigen quantitative test kit (Autobio, CL0310)
3. Consumables and Instruments:
    96-well cell culture plate (Cornin-3599)
    $CO_2$ incubator (HERA-CELL-240)
    Optical sealing film (ABI-4311971)
    Quantitative PCR 96-well plate (Applied Biosystems-4306737)
    Fluorescence quantitative PCR instrument (Applied Biosystems-7500 real time PCR system)
Experimental Methods:
1. HepG2.2.15 cells (4×10$^4$ cells/well) were seeded to a 96-well plate and cultured overnight at 37° C., 5% $CO_2$.
2. On the day 2, the compound was diluted to a total of 8 concentrations, with a 3-fold gradient dilution. Different concentrations of compounds were added into the culture wells in duplicate wells. The final concentration of DMSO in the culture medium was 0.5%. 10 μM ETV (Entecavir) was used as a 100% inhibition control; 0.5% DMSO was used as a 0% inhibition control.
3. On the day 5, the culture medium was replaced with fresh culture medium containing the compound.
4. On the day 8, the culture medium in the culture wells was collected, and some samples were taken for ELISA to determine the content of hepatitis B virus S antigen; some samples were taken for DNA extraction using the high-throughput DNA purification kit (Qiagen-51162).
5. The preparation of PCR reaction solution is shown in Table 1:

TABLE 2

Preparation of PCR reaction solution

| Item | Volume required for 1 well (μL) | Volume required for 80 wells (μL) |
|---|---|---|
| Quantitative quick start universal probe reagent | 12.5 | 1000 |
| Forward primer (10 μmol) | 1 | 80 |
| Reverse primer (10 μmol) | 1 | 80 |
| Probe (10 μmol) | 0.5 | 40 |

```
Forward primer sequence:
                                (SEQ ID NO. 1)
GTGTCTGCGGCGTTTTATCA Reverse primer sequence:
                                (SEQ ID NO. 2)
GACAAACGGGCAACATACCTT Probe sequence:
                                (SEQ ID NO. 3)
5' + FAM + CCTCTKCATCCTGC

TGCTATGCCTCATC + TAMRA-3'
```

6. 15 μL of reaction mixture was added to each well of a 96-well PCR plate, and then 10 μL of sample DNA or HBV DNA standard was added to each well.
7. The reaction settings for PCR are as follows: heating at 95° C. for 10 minutes; followed by denaturation at 95° C. for 15 seconds, and extension at 60° C. for 1 minute, for a total of 40 cycles.
8. Content determination of hepatitis B virus surface antigen by ELISA
50 μL of sample and standard were added into a reaction plate respectively, followed by addition of 50 μL of enzyme conjugate into each well. The mixture was shaking to mix well, then placed in a bath at 37° C. for 60 min. The plate was then washed 5 times with washing solution, followed by addition of 50 μL of illuminating substrate into each well and mix well. The reaction was performed at room temperature for 10 min in the dark. Chemoluminescence intensity was determined by an ELISA finally.
9. Data analysis:
Calculation of the percentage of inhibition: % Inh.=(1-value of the sample/value of DMSO control)×100.
Calculation of $EC_{50}$: The 50% inhibitory concentration ($EC_{50}$) of the compound against HBV was calculated by GraphPad Prism software.
Results of the experiment: the $EC_{50}$ of the compound of formula (I) against HBV-DNA and HBsAg were 2.55 nM and 3.88 nM respectively.
Conclusions of the experiment: the compound of formula (I) of the present disclosure can inhibit HBV-DNA and hepatitis B surface antigen (HBsAg) effectively.

Example 4 In Vivo Efficacy Study of the Compound of Formula (I)

Experimental Materials:
C57BL/6 mice, 10% HP-β-CD as vehicle, TDF (Tenofovir dipivoxil) as refer compound, the compound of formula (I), and recombinant virus rAAV8-1.3HBV.
The reagents of the present project mainly included QIAamp96 DNA kit and TaqMan® Universal PCR Master Mix, hepatitis B surface antigen test kit.
The instrument included centrifuge (Beckman Allegra X-15R), tissue grinder (QIAGEN-Tissue lyser II) and spectrophotometer (Thermo-NANODROP 1000).
Experimental Methods:
a) All mice were administrated orally on the day 28 after being injected with virus, the day of administration was designated as day 0. Before administration, serum was collected by submandibular blood sampling for all mice. The mice were administration once a day for four weeks. The detailed dosage regimen was shown in Table 3.
b) Serum was collected by submandibular blood sampling for all mice twice a week, with each sampling volume being approximately 100 μL. The detailed blood sampling time is shown in Table 3.
c) On the day 28, all mice were euthanized and the blood was collected from the heart for serum collection.
d) All serum samples were sent for analysis.

TABLE 3 in vivo experimental protocol

| Group | No. of mice | Compound | Dosage (mg/kg) | Dosage volume (mL/kg) | Dosage regimen | Serum collection regimen |
|---|---|---|---|---|---|---|
| 1 | 5 | mock | / | 10 | The 28th day after virus injection was designated as day 0, administration is performed once a day for | The 28th day after virus injection was designated as day 0, blood collection is performed twice a week, |
| 2 | 5 | tenofovir disoprox | 1 | | | |
| 3 | 5 | RG7834 | 10 | | | |
| 4 | 5 | the compound of formula (I) | 3 | | | |
| 5 | 5 | the compound of formula (I) | 10 | | | |

TABLE 3-continued in vivo experimental protocol

Dosage design

| Group | No. of mice | Compound | Dosage (mg/kg) | Dosage volume (mL/kg) | Dosage regimen | Serum collection regimen |
|---|---|---|---|---|---|---|
| 6 | 5 | the compound of formula (I) | 30 | | four weeks, e.g. the time for each administration is the day 0-27. | and the volume of which is about 100 μL. The time for each blood collection is the day 3, 7, 10, 14, 17, 21, 24, and 28. |
| 7 | 5 | the compound of formula (I) + TDF | (10 mg/kg + 1 mg/kg) | | | |

Figure 4:
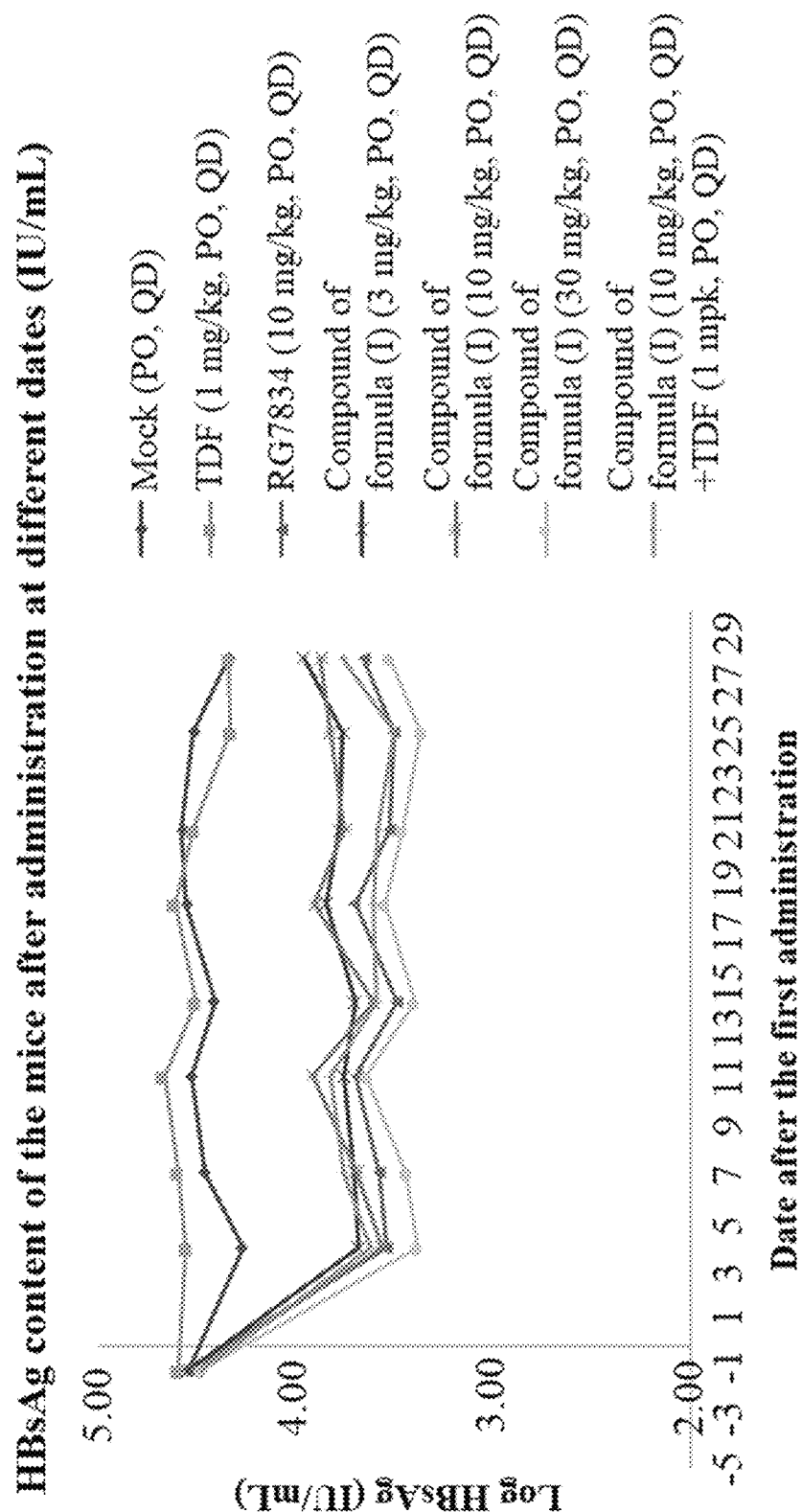
FIG. 4 is the HBsAg content (IU/mL) of mice at different dates after administration.
Figure 5:
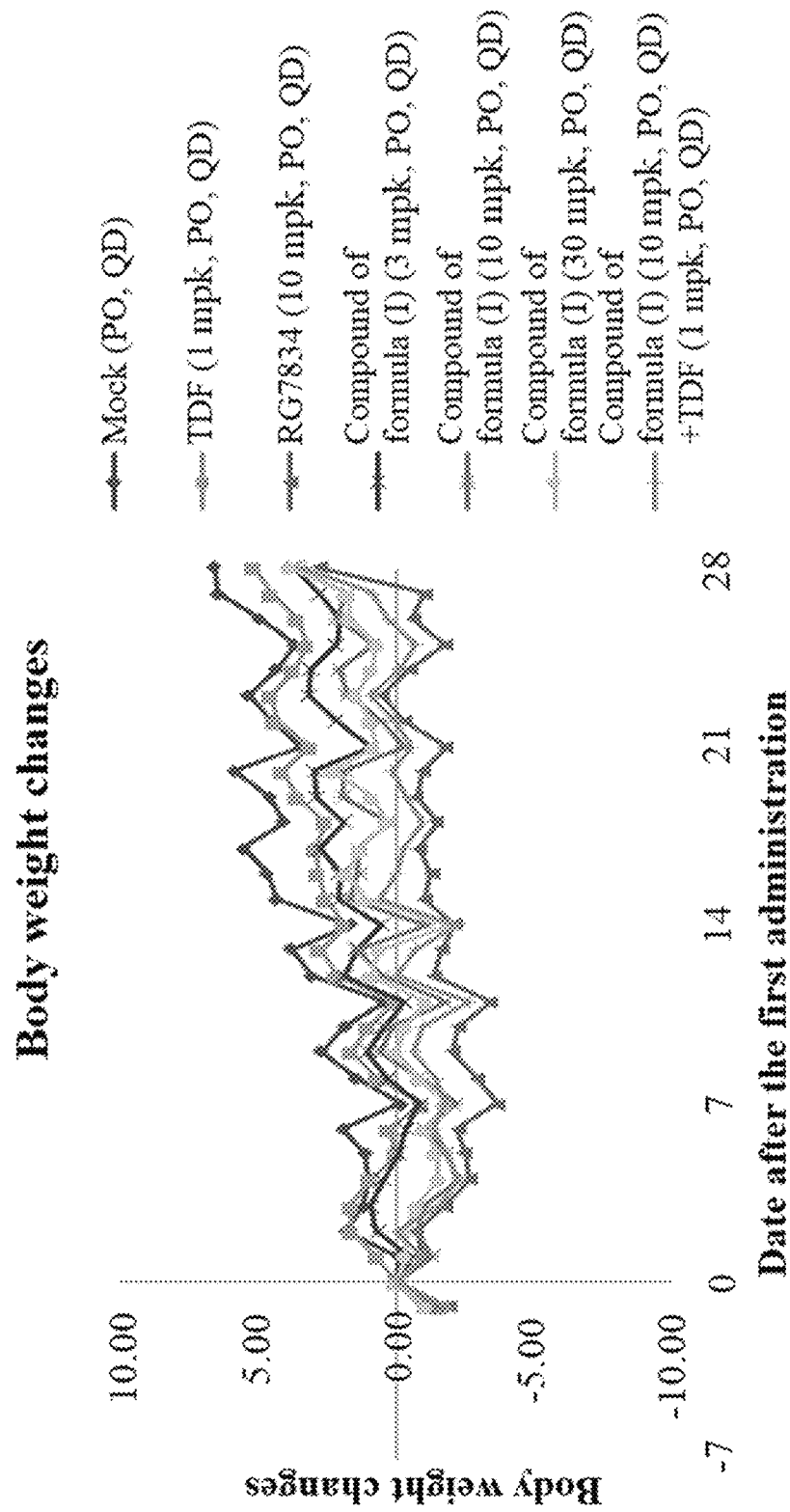
FIG. 5 is the changes in bodyweight of mice at different dates after administration.

Results of the Experiment:

The anti-HBV activity of the test compound in AAV/HBV mice model was evaluated by determining the content of HBsAg in the serum of the mice. The results are shown in Table 4 and FIG. 4. The changes in body weight of the mice are shown in FIG. 5.

TABLE 4

HBsAg content in mice on different dates after administration (IU/mL)

| Detection date (day) | Mock (PO, QD) | TDF (1 mg/kg, PO, QD) | RG7834 (10 mg/kg, PO) | the compound of formula (I) (3 mg/kg, PO) | the compound of formula (I) (10 mg/kg, PO) | the compound of formula (I) (30 mg/kg, PO) | the compound of formula (I) (10 mg/kg, PO) + TDF(1 mg/kg, PO, QD) |
|---|---|---|---|---|---|---|---|
| −1 | 4.54 | 4.59 | 4.56 | 4.54 | 4.51 | 4.48 | 4.48 |
| 4 | 4.27 | 4.56 | 3.54 | 3.68 | 3.56 | 3.38 | 3.62 |
| 7 | 4.46 | 4.59 | 3.58 | 3.70 | 3.69 | 3.44 | 3.76 |
| 11 | 4.52 | 4.66 | 3.70 | 3.76 | 3.92 | 3.64 | 3.82 |
| 14 | 4.41 | 4.50 | 3.49 | 3.70 | 3.61 | 3.40 | 3.59 |
| 18 | 4.56 | 4.61 | 3.70 | 3.85 | 3.90 | 3.55 | 3.61 |
| 21 | 4.58 | 4.52 | 3.52 | 3.78 | 3.75 | 3.46 | 3.58 |
| 25 | 4.52 | 4.33 | 3.50 | 3.76 | 3.83 | 3.37 | 3.50 |
| 28 | 4.34 | 4.34 | 3.66 | 3.96 | 3.87 | 3.53 | 3.76 |

Conclusions of the Experiment:

In the AAV/HBV mice model, the compound of the present disclosure was able to reduce HBsAg significantly, and mice performed good tolerance.

What is claimed is:

1. A crystal form A of a compound represented by formula (I), wherein the crystal form A has a X-ray powder diffraction pattern comprising characteristic diffraction peaks with the following angles 2θ: 8.04°±0.2°, 16.52°±0.2° and 19.52°±0.2°,

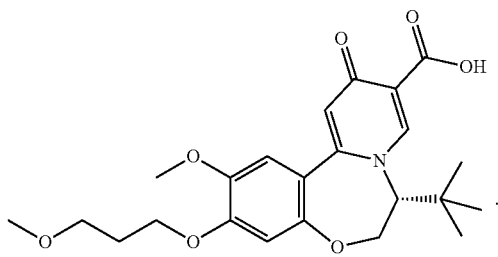

2. The crystal form A of claim 1, wherein the X-ray powder diffraction pattern comprises characteristic diffraction peaks with the following angles 2θ: 8.04°±0.2°, 10.47°±0.2°, 11.90°±0.2°, 16.52°±0.2°, 18.06°±0.2°, 19.52°±0.2°, 22.02°±0.2° and 25.28°±0.2°.

3. The crystal form A of claim 1 having a differential scanning calorimetry curve with an onset of endothermic peak at 139.64±5° C.

4. The crystal form A of claim 1 having a thermogravimetric analysis curve with a weight loss of 0.4757% at 125.23±3° C.

5. The crystal form A of claim 2 having a differential scanning calorimetry curve with an onset of endothermic peak at 139.64±5° C.

6. The crystal form A of claim 2 having a thermogravimetric analysis curve with a weight loss of 0.4757% at 125.23±3° C.

* * * * *